United States Patent
Sang et al.

(10) Patent No.: US 10,550,060 B2
(45) Date of Patent: *Feb. 4, 2020

(54) PROCESS FOR THE DIRECT CONVERSION OF ALKENES TO CARBOXYLIC ACIDS

(71) Applicant: EVONIK DEGUSSA GMBH, Essen (DE)

(72) Inventors: Rui Sang, Liaocheng (CN); Peter Kucmierczyk, Herne (DE); Kaiwu Dong, Bo Zhou (CN); Ralf Jackstell, Rostock (DE); Matthias Beller, Osteebad Nienhagen (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/215,991

(22) Filed: Dec. 11, 2018

(65) Prior Publication Data

US 2019/0194110 A1 Jun. 27, 2019

(30) Foreign Application Priority Data

Dec. 21, 2017 (EP) .................................. 17209348

(51) Int. Cl.
| | | |
|---|---|---|
| *C07C 51/14* | (2006.01) | |
| *B01J 31/00* | (2006.01) | |
| *B01J 31/22* | (2006.01) | |
| *B01J 31/24* | (2006.01) | |
| *B01J 31/30* | (2006.01) | |
| *C07B 41/08* | (2006.01) | |

(52) U.S. Cl.
CPC ........... *C07C 51/14* (2013.01); *B01J 31/2234* (2013.01); *B01J 31/2295* (2013.01); *B01J 31/2409* (2013.01); *B01J 31/30* (2013.01); *B01J 2231/321* (2013.01); *B01J 2531/842* (2013.01); *C07B 41/08* (2013.01)

(58) Field of Classification Search
CPC .. C07C 51/14; C07C 53/128; B01J 2231/321; B01J 31/2234
See application file for complete search history.

(56) References Cited

U.S. PATENT DOCUMENTS

| 8,445,711 B2 | 5/2013 | Eastham et al. |
| 9,040,445 B2 * | 5/2015 | Eastham .............. B01J 31/0225 502/162 |
| 9,938,310 B2 | 4/2018 | Dong et al. |
| 2018/0022686 A1 | 1/2018 | Fang et al. |
| 2018/0022773 A1 | 1/2018 | Dong et al. |

FOREIGN PATENT DOCUMENTS

| DE | 196 21 967 A1 | 12/1997 |
| EP | 3 272 733 A1 | 1/2018 |
| EP | 3 272 759 A1 | 1/2018 |
| EP | 3 272 760 A1 | 1/2018 |
| WO | 2006/066975 A1 | 6/2006 |

OTHER PUBLICATIONS

U.S. Appl. No. 16/188,995, Sang et al., filed Nov. 13, 2018.
U.S. Appl. No. 16/189,029, Sang et al., filed Nov. 13, 2018.
U.S. Appl. No. 16/216,004, Sang et al., filed Dec. 11, 2018.
U.S. Appl. No. 16/216,020, Sang et al., filed Dec. 11, 2018.
U.S. Appl. No. 16/216,037, Sang et al., filed Dec. 11, 2018.
U.S. Appl. No. 16/216,053, Sang et al., filed Dec. 11, 2018.
European Search Report dated Jun. 22, 2018 in EP 17 20 9348 (7 pages).

* cited by examiner

*Primary Examiner* — Sikarl A Witherspoon
(74) *Attorney, Agent, or Firm* — Smith, Gambrell & Russell, LLP

(57) ABSTRACT

Process for the direct conversion of alkenes to carboxylic acids.

9 Claims, No Drawings

PROCESS FOR THE DIRECT CONVERSION OF ALKENES TO CARBOXYLIC ACIDS

The invention relates to a process for the direct conversion of alkenes to carboxylic acids.

Carboxylic acids are used in the preparation of polymers, pharmaceuticals, solvents and food additives. The routes leading to carboxylic acids generally include the oxidation of hydrocarbons, alcohols or aldehydes, the oxidative cleavage of olefins by ozonolysis, the hydrolysis of triglycerides, nitriles, esters or amides, the carboxylation of Grignard or organolithium reagents, and the halogenation and subsequent hydrolysis of methyl ketones in the haloform reaction.

The object of the invention was to provide a process with which alkenes can be directly converted to a carboxylic acid.

In the context of this application, "direct conversion" is intended to mean that the reaction takes place in one step, i.e. without separation or work-up or similar of an intermediate product.

This does not exclude, in the course of the reaction, intermediates forming which are directly converted onward.

The object is achieved by a process according to claim 1.

Process comprising the process steps of:

a) addition of an alkene:

b) addition of a complex, comprising a compound according to structure (1) and also Pd, or a compound according to structure (1) and a substance comprising Pd

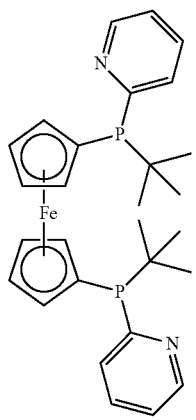

(1)

c) feeding in CO;

d) heating the reaction mixture such that the alkene is converted to a carboxylic acid, wherein the alkene is directly converted to the carboxylic acid.

In a variant of the process, the substance in process step b) is selected from: $PdCl_2$, $PdBr_2$, $Pd(acac)_2$, $Pd(dba)_2$ (dba=dibenzylideneacetone), $PdCl_2(CH_3CN)_2$.

In a variant of the process, the substance in process step b) is $Pd(acac)_2$.

In a variant of the process, the process comprises the additional process step e):

e) addition of acetic acid.

In a variant of the process, the process comprises the additional process step f):

f) addition of water.

In a variant of the process, the process comprises the additional process step g):

g) addition of p-toluenesulfonic acid (PTSA).

In a variant of the process, the reaction mixture is heated to a temperature in the range from 80° C. to 160° C. in process step d).

In a preferred variant of the process, the reaction mixture is heated to a temperature in the range from 100° C. to 140° C. in process step d).

In a variant of the process, the CO is fed in in process step c) such that the reaction proceeds under a CO pressure in the range from 20 bar to 60 bar.

In a preferred variant of the process, the CO is fed in in process step c) such that the reaction proceeds under a CO pressure in the range from 30 bar to 50 bar.

The invention is more particularly elucidated hereinbelow with reference to working examples.

Variation of the Ligand

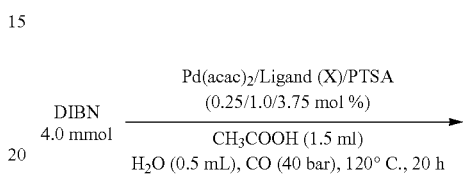

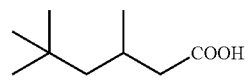

(1)

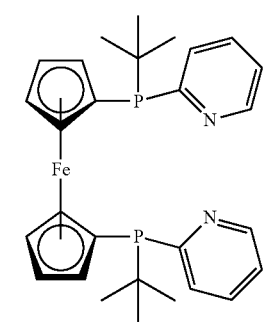

(2)

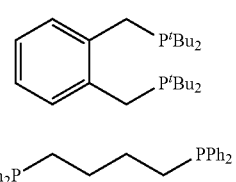

(3)

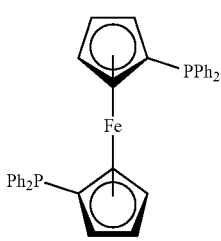

(4)

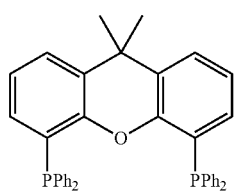

(5)

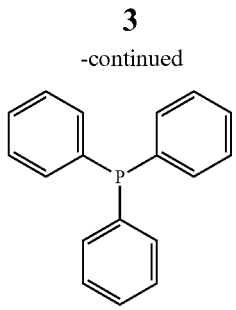

(6)

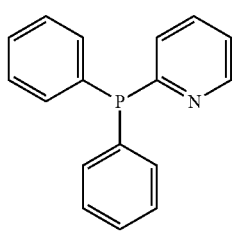

(7)

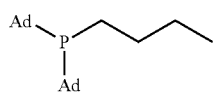

(8)

A 4 ml vial was charged with [Pd(acac)₂] (3.05 mg, 0.25 mol %), ligand (X) (1.0 mol %), para-toluenesulfonic acid (28.5 mg, 3.75 mol %) and an oven-dried stirrer bar. The vial was then sealed with septa (PTFE-coated styrene-butadiene rubber) and a phenol resin cap. The vial was evacuated and refilled with argon three times. H₂O (0.5 ml), acetic acid (1.5 ml) and diisobutene (DIBN) (4.0 mmol) were added to the vial with a syringe. The vial was placed in an alloy plate, which was transferred to an autoclave (300 ml) of the 4560 series from Parr Instruments under argon atmosphere. After flushing the autoclave three times with CO, the pressure of CO was increased to 40 bar at room temperature. The reaction was conducted at 120° C. for 20 h. On conclusion of the reaction, the autoclave was cooled down to room temperature and cautiously decompressed. Isooctane (100 μl) was then added as internal standard. Conversion was measured by GC analysis.

The above-described experiment was carried out with variation of the ligand (X), with X=1 to 8.

The results are compiled in the following table 1;

TABLE 1

| Ligand | Yield % |
|---|---|
| (1)* | >99 |
| (2) | 7 |
| (3) | 39 |
| (4) | 26 |
| (5) | 16 |
| (6) | 8 |
| (7) | 13 |
| (8) | 29 |

* inventive process

Variation of the Alkene

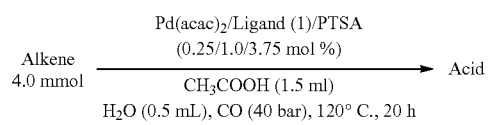

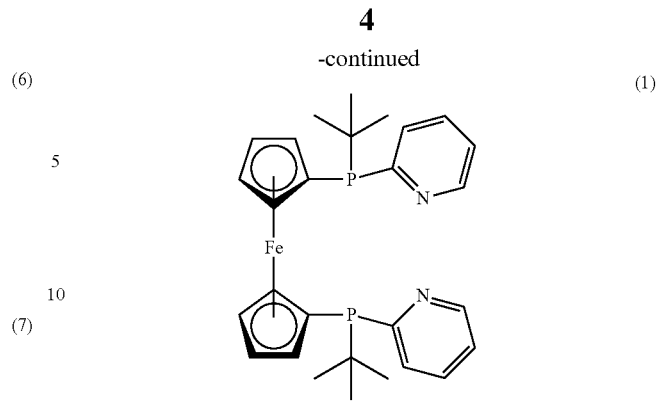

(1)

A 4 ml vial was charged with [Pd(acac)₂] (3.07 mg, 0.25 mol %), ligand (1) (20.64 mg, 1.0 mol %), p-toluenesulfonic acid (28.5 mg, 3.75 mol %) and an oven-dried stirrer bar. The vial was then sealed with septa (PTFE-coated styrene-butadiene rubber) and a phenol resin cap. The vial was then connected to the atmosphere with a needle. The vial was evacuated and refilled with argon three times. H₂O (0.5 ml), acetic acid (1.5 ml) and alkene (4.0 mmol) were added to the vial with a syringe. The vial was placed in an alloy plate, which was transferred to an autoclave (300 ml) of the 4560 series from Parr Instruments under argon atmosphere. After flushing the autoclave three times with CO, the pressure of CO was increased to 40 bar at room temperature. The reaction was conducted at 120° C. for 20 h. On conclusion of the reaction, the autoclave was cooled down to room temperature and cautiously decompressed. Isooctane (100 μl) was then added as internal standard. Conversion was measured by GC analysis.

The experiment described above was repeated with variation of the alkene.

The results are compiled in the following table 2:

TABLE 2

| Alkene | Acid | Yield |
|---|---|---|
|  |  | 99% |
|  | 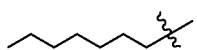 | 98%, n/iso mixture |
|  | 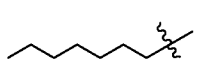 | 97%, iso mixture |
| 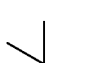 | 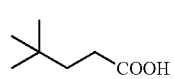 | 99% |
|  | 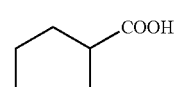 | 80% |
| 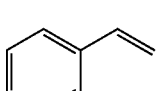 | 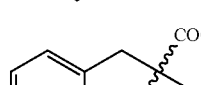 | 95%, n/iso mixture |
| 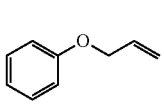 | 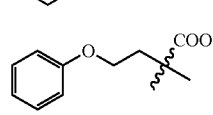 | 94%, n/iso mixture |

As the experimental results show, the object is achieved by a process according to the invention.

The invention claimed is:

1. A process for the direct conversion of alkene to the corresponding carboxylic acid comprising:
   a) adding an alkene, forming a reaction mixture;
   b) adding a complex, comprising a compound according to structure (1) and also Pd,
   or a compound according to structure (1) and a substance comprising Pd

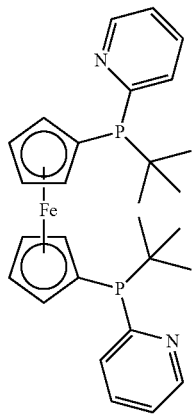

(1)

c) feeding in CO;
   d) heating the reaction mixture such that the alkene and CO are directly to the corresponding carboxylic acid.

2. The process according to claim 1, wherein the substance in process step b) is PdCl$_2$, PdBr$_2$, Pd(acac)$_2$, Pd(dba)$_2$ (dba=dibenzylideneacetone) or PdCl$_2$(CH$_3$CN)$_2$.

3. The process according to claim 1, wherein the process comprises the additional process step e):
   e) addition of acetic acid.

4. The process according to claim 1, wherein the process comprises additional process step f):
   f) addition of water.

5. The process according to claim 1, wherein the process comprises the additional process step g):
   g) addition of p-toluenesulfonic acid.

6. The process according to claim 1, wherein the reaction mixture is heated to a temperature in the range from 80° C. to 160° C. in process step d).

7. The process according to claim 1, wherein the CO is fed in in process step c) such that the reaction proceeds under a CO pressure in the range from 20 bar to 60 bar.

8. The process of claim 1 wherein the corresponding carboxylic acid is an iso or n/iso mixture.

9. The process of claim 1 wherein the alkene is cyclic or acyclic compound and the acyclic carbon-carbon double bond is characterized as primary and the corresponding carboxylic acid is a mixture.

* * * * *